(12) United States Patent
Choi et al.

(10) Patent No.: US 8,661,654 B2
(45) Date of Patent: Mar. 4, 2014

(54) METHOD FOR MANUFACTURING A SPIRAL COIL

(75) Inventors: Myoung Seon Choi, Daegu (KR); Sung Joon Kim, Daegu (KR); Won Nyoung Heo, Daegu (KR)

(73) Assignee: Industry-Academic Cooperation Foundation, Yeungnam University, Gyeongsan-Si, Gyeongsangbuk-Do (KR)

( * ) Notice: Subject to any disclaimer, the term of this patent is extended or adjusted under 35 U.S.C. 154(b) by 71 days.

(21) Appl. No.: 13/320,615

(22) PCT Filed: Jun. 24, 2009

(86) PCT No.: PCT/KR2009/003407
§ 371 (c)(1),
(2), (4) Date: Nov. 15, 2011

(87) PCT Pub. No.: WO2010/131794
PCT Pub. Date: Nov. 18, 2010

(65) Prior Publication Data
US 2012/0063631 A1 Mar. 15, 2012

(30) Foreign Application Priority Data
May 15, 2009 (KR) ........................ 10-2009-0042718

(51) Int. Cl.
*H01F 7/06* (2006.01)

(52) U.S. Cl.
USPC ............ 29/605; 29/592.1; 29/602.1; 29/606; 257/531; 336/65; 336/83; 336/200; 336/220; 336/233; 381/396

(58) Field of Classification Search
USPC ............ 29/592.1, 602.1, 605, 606; 257/531; 336/65, 83, 200, 206–208, 220, 223, 336/232, 233; 381/396
See application file for complete search history.

(56) References Cited

U.S. PATENT DOCUMENTS

| 4,264,789 A | | 4/1981 | Kaizu et al. |
| 4,281,223 A | | 7/1981 | Ugaji et al. |
| 4,406,321 A | * | 9/1983 | Fujiwara et al. ............... 164/504 |
| 4,816,784 A | * | 3/1989 | Rabjohn ..................... 333/24 R |
| 5,225,969 A | * | 7/1993 | Takaya et al. .................. 361/795 |
| 5,655,665 A | * | 8/1997 | Allen et al. .................. 209/223.1 |
| 5,781,071 A | * | 7/1998 | Kusunoki ..................... 330/269 |
| 6,580,334 B2 | * | 6/2003 | Simburger et al. .......... 333/24 R |
| 6,801,114 B2 | * | 10/2004 | Yang et al. .................... 336/200 |
| 7,174,024 B1 | | 2/2007 | Suzuki et al. |
| 2005/0231434 A1 | | 10/2005 | Azadegan et al. |

FOREIGN PATENT DOCUMENTS

| JP | 2000-088816 | 3/2000 |
| JP | 2003-319493 | 11/2003 |
| JP | 2006-208325 | 8/2006 |

* cited by examiner

Primary Examiner — Paul D Kim
(74) Attorney, Agent, or Firm — Sherr & Jiang, PLLC

(57) ABSTRACT

A method for manufacturing a spiral coil, the method including: forming a solenoid having a diameter larger than a length by spirally winding an insulated electric wire; forming a spiral coil having folded corners by folding four corners in a circumference direction with respect to the solenoid; fixing the folded corners of the spiral coil; and fixing two terminal portions corresponding to start and end points of the spiral coil to a fixing module. According to the method, a thin and long spiral coil having folded corners is easily manufactured by using a general insulated electric wire. In addition, the spiral coil manufactured by using such a method is applicable to a surface radio frequency (RF) coil optimized for various applications of an electro-magnetic acoustic transducer (EMAT) and enables easy access to an optimized transducer.

4 Claims, 8 Drawing Sheets

METHOD FOR MANUFACTURING A SPIRAL COIL

CROSS REFERENCE TO PRIOR APPLICATIONS

This application is a National Stage Patent Application of PCT International Patent Application No. PCT/KR2009/003407 (filed on Jun. 24, 2009) under 35 U.S.C. §371, which claims priority to Korean Patent Application No. 10-2009-0042718 (filed on May 15, 2009), which are all hereby incorporated by reference in their entirety.

BACKGROUND OF THE INVENTION

1. Field of the Invention

The present invention relates to a method for manufacturing a spiral coil, the spiral coil, and an electro-magnetic acoustic transducer (EMAT) including the same, and more particularly, to a method for manufacturing a spiral coil used in an EMAT, the spiral coil, and an EMAT including the same.

2. Description of the Related Art

Electro-magnetic acoustic transducers (EMATs) widely used in nondestructive inspection fields are classified into two types by ultrasonic wave generation mechanism, i.e., into Lorentz force transducers and magnetostrictive transducers. The Lorentz force transducers use interference between a static magnetic field and an eddy current in a conductive material, and the magnetostrictive transducers use dimension change (magnetostriction) of a ferromagnetic material due to superimposition of a bias static magnetic field and a dynamic magnetic field. The static magnetic field is provided to a material by a permanent magnet or electromagnet, and the eddy current and dynamic magnetic field are provided to a material by a coil operated by an alternating current (AC) pulse in a radio frequency (RF) band, i.e., an RF coil. Ultrasonic waves are generated near a surface of the material due to a skin effect of the eddy current and dynamic magnetic field, and a mode thereof is adjusted by a relative direction of the static magnetic field and eddy current (or dynamic magnetic field). During a receiving process, the RF coil detects a change of magnetic flux aroused in the material by the ultrasonic waves. When a target material is a conductive material or ferromagnetic material, the target material may be used as an element of a transducer so as to generate and detect ultrasonic waves in the target material without having to directly contact the target material to other two elements (RF coil and bias magnet) of the transducer. When the target material is a nonconductive material or nonmagnetic material, ultrasonic waves may be transmitted or received by temporarily or permanently adhering a thin strip having an excellent transducing characteristic to the target material. The thin strip approach may also be used with a target of a conductive or ferromagnetic material for efficient ultrasonic wave transmission and reception.

FIG. 1 schematically illustrates an elongated spiral surface RF coil (having large slenderness) widely used for various EMATs generating or detecting longitudinal waves, transverse waves, or guided waves. When the elongated spiral surface RF coil is used, an EMAT is designed such that an ultrasonic transmitting and receiving area is limited to two parallel leg portions of the elongated spiral surface RF coil. A current optimum method for manufacturing a spiral coil uses a printed circuit technology. The printed circuit technology enables manufacturing of a coil that is very accurate, thin, and flexible, but requires expensive devices. Hirao and Ogi's writings describe in detail about manual manufacturing processes from an enamel copper wire to a spiral surface coil. Such manual manufacturing processes for manufacturing a spiral surface coil are particularly suitable for manufacturing a small coil. However, as a size of spiral surface coil increases, manufacturing costs are remarkably increase or accuracy is deteriorated. Thus, magnetostrictive guided wave transducers used for long-range ultrasonic test of a large structure use a solenoid that has lower guided wave transmitting and receiving efficiency than a spiral surface coil. The solenoid is not a surface coil. Accordingly, the solenoid includes a connector electrically connecting adjacent loops for easy installation to a surface of the large structure, which makes it difficult to variously apply coils having an optimized wound number.

SUMMARY OF THE INVENTION

The present invention provides a method for manufacturing a spiral coil having accuracy enough to be used for an electro-magnetic acoustic transducer (EMAT), the spiral coil, and an EMAT including the same.

According to an aspect of the present invention, there is provided a method for manufacturing a spiral coil, the method including: forming a solenoid having a diameter larger than a length by spirally winding an insulated electric wire; forming a spiral coil having folded corners by folding four corners in a circumference direction with respect to the solenoid; fixing the folded corners of the spiral coil; and fixing two terminal portions corresponding to start and end points of the spiral coil.

The forming of the solenoid may include: preparing a work module including a work plate having a plurality of thread grooves along a length direction, and two cylinders having screw threads at terminals to be respectively lockable to the plurality of thread grooves; respectively locking the two cylinders to two thread grooves having a separation distance corresponding to a leg length of the spiral coil, which are selected from among the plurality of thread grooves; forming the solenoid by spirally firmly winding the insulated electric wire along the two cylinders; and adhering an adhesive tape along external and internal surfaces of the solenoid so as to fix a wound shape of the solenoid, and the forming of the spiral coil having the folded corners may include forming a spiral coil having a plane shape by respectively folding the four corners in the circumference direction with respect to the solenoid fixed by the adhesive tape.

The fixing of the folded corners of the spiral coil may include: exposing a top surface of the spiral coil upward by fixing a bottom surface of the spiral coil having the plane shape to a top surface of a platform; removing a part of the adhesive tape, which is adhered to the top surface of the spiral coil; covering and adhering a first single-sided adhesive tape to the top surface of the spiral coil; exposing a bottom surface of the spiral coil upward by turning over the spiral coil at the platform; removing a part of the adhesive tape, which is adhered to the bottom surface of the spiral coil; covering and adhering a second single-sided adhesive tape to the bottom surface of the spiral coil; and completing the spiral coil by removing the spiral coil from the platform and then trimming edges of the first and second single-sided adhesive tapes.

According to another aspect of the present invention, there is provided a method for manufacturing a spiral coil, the method including: forming a solenoid having a diameter larger than a length by spirally winding an insulated electric wire; forming a U-shaped ribbon cable having two cut ends and folded corners by cutting a part of the solenoid in a length direction of the solenoid and folding two corners in a circumference direction of the solenoid; fixing the folded corners of the U-shaped ribbon cable; removing insulated films at the ends of the insulated electric wires at the two cut ends; transforming the U-shaped ribbon cable to a U-shaped ribbon cable formed of quasi-rectangular wires by dividing ends of internal wires exposed by removing the insulated films into a plurality of bundles and forming each of the plurality of bundles to a quasi-rectangular wire by soldering the ends of the internal wires according to bundles; forming a spiral coil by connecting the quasi-rectangular wires at one cut end and the quasi-rectangular wires at another cut end according to lines, wherein quasi-rectangular wires corresponding to two terminal portions pertaining to start and end points of the spiral coil are not connected; and fixing the two terminal portions.

The forming of the U-shaped ribbon cable may include: forming a ribbon cable having two cut ends by cutting a part of the solenoid in a length direction of the solenoid; and forming the U-shaped ribbon cable having folded corners by folding two corners in a circumference direction of the ribbon cable.

According to another aspect of the present invention, there is provided a spiral coil having folded corners, which is manufactured by using the method above. Also, according to another aspect of the present invention, there is provided an electro-magnetic acoustic transducer (EMAT) comprising a spiral coil having folded corners, wherein the spiral coil is manufactured by using the method above.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Hereinafter, the present invention will be described more fully with reference to the accompanying drawings, in which exemplary embodiments of the invention are shown.

Figure 1:
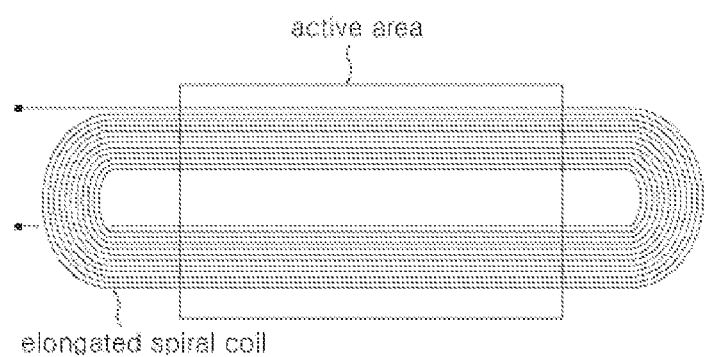
FIG. 1 is a schematic diagram of an elongated spiral coil generally used in conventional electro-magnetic acoustic transducer (EMAT) fields.
Figure 2:
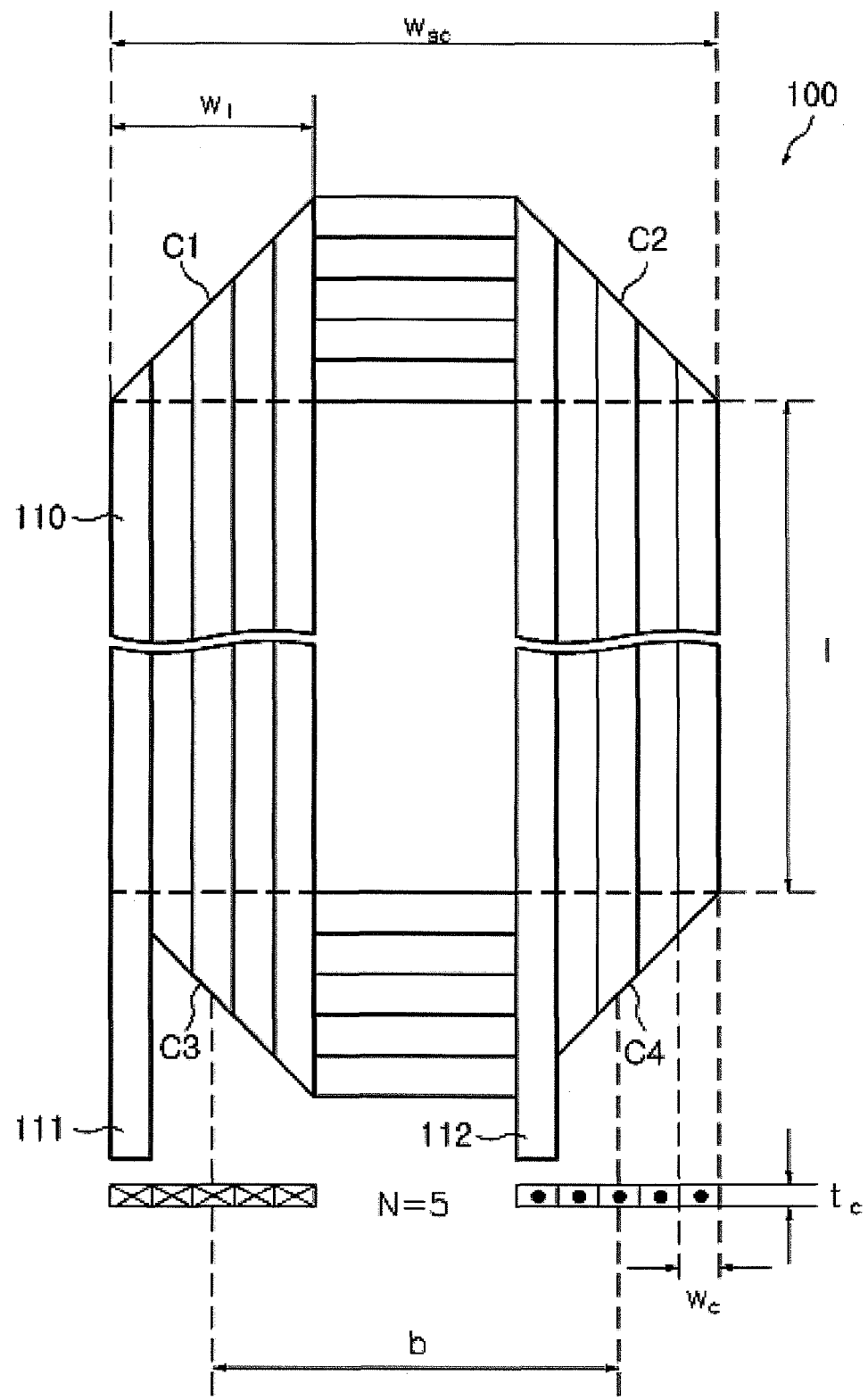
FIG. 2 is a plan view of a spiral coil manufactured according to an embodiment of the present invention.
Figure 3A:
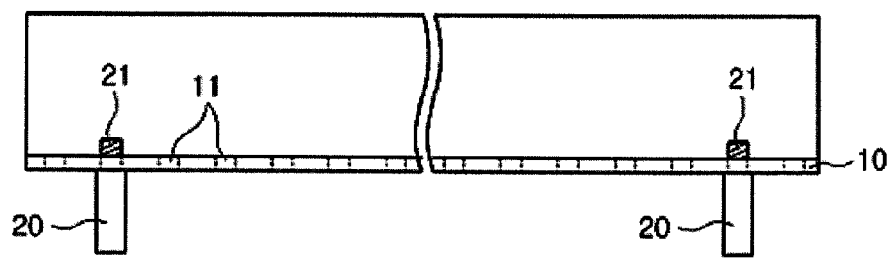
FIGS. 3A and 3B are respectively a plan view and a front view of a work module for generating the spiral coil of FIG. 2.
Figure 3B:
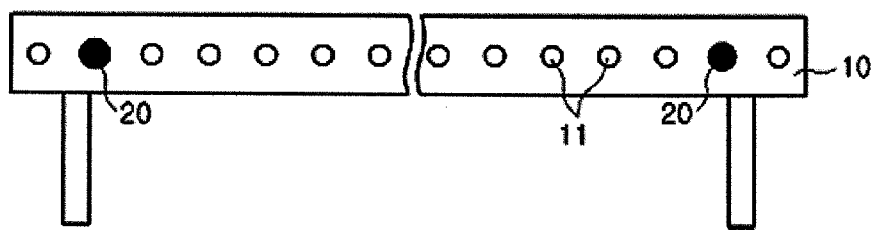
Figure 4:
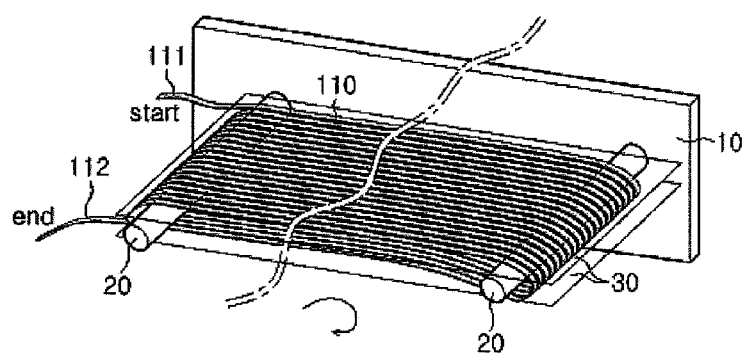
FIG. 4 is a perspective view for describing a process of forming a solenoid for the spiral coil of FIG. 2 by using the work module of FIG. 3.
Figure 5:
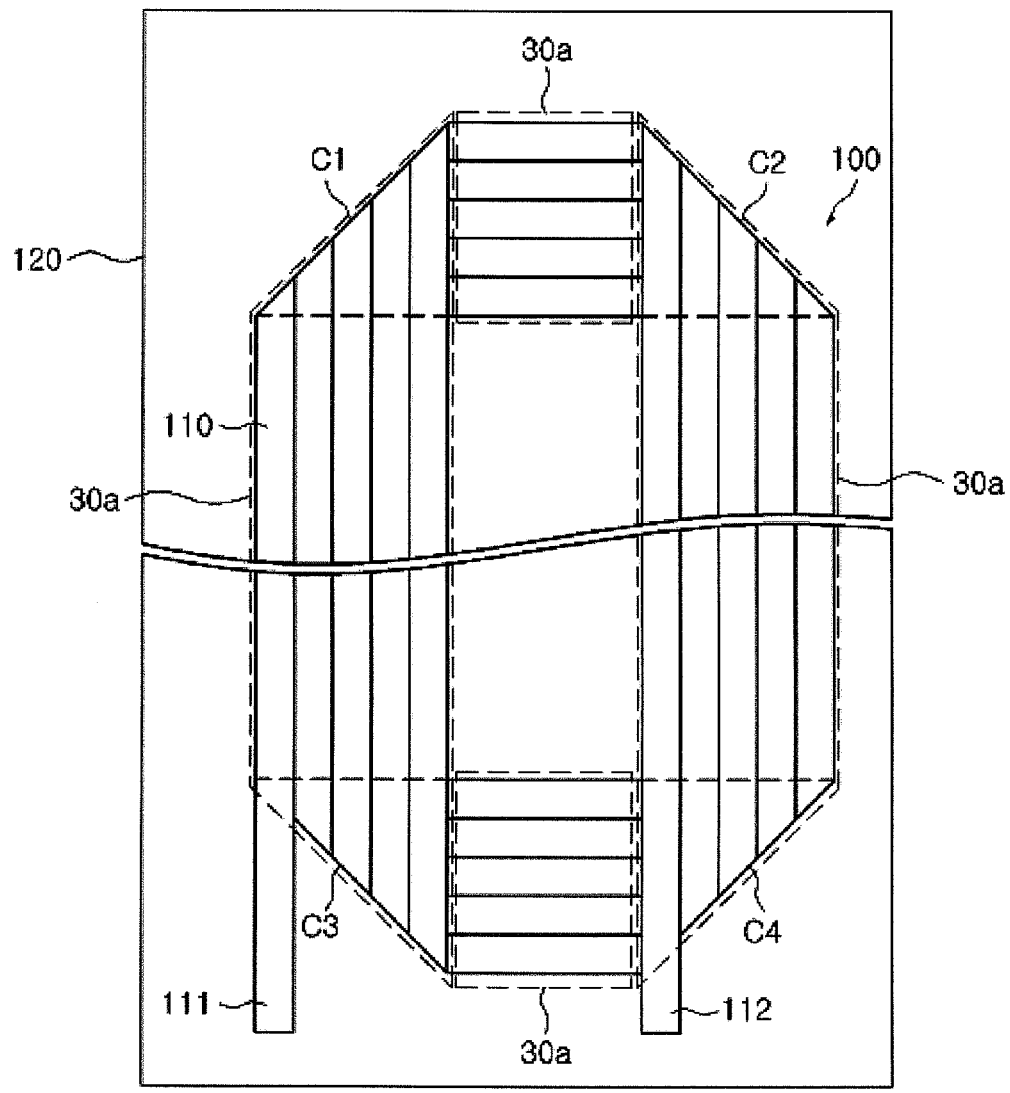
FIGS. 5 and 6 are plan views for describing manufacturing processes of the spiral coil of FIG. 2.
Figure 6:
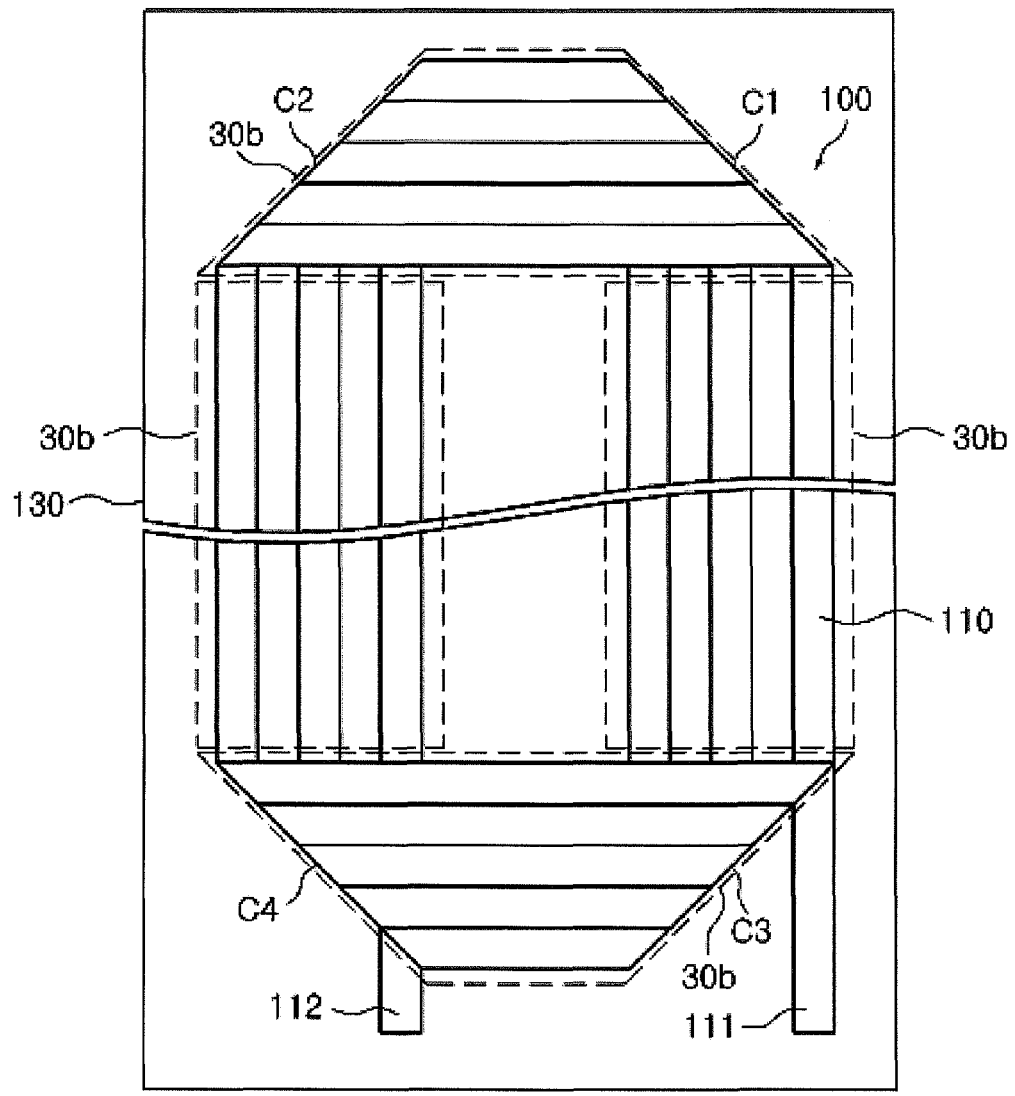
Figure 7:
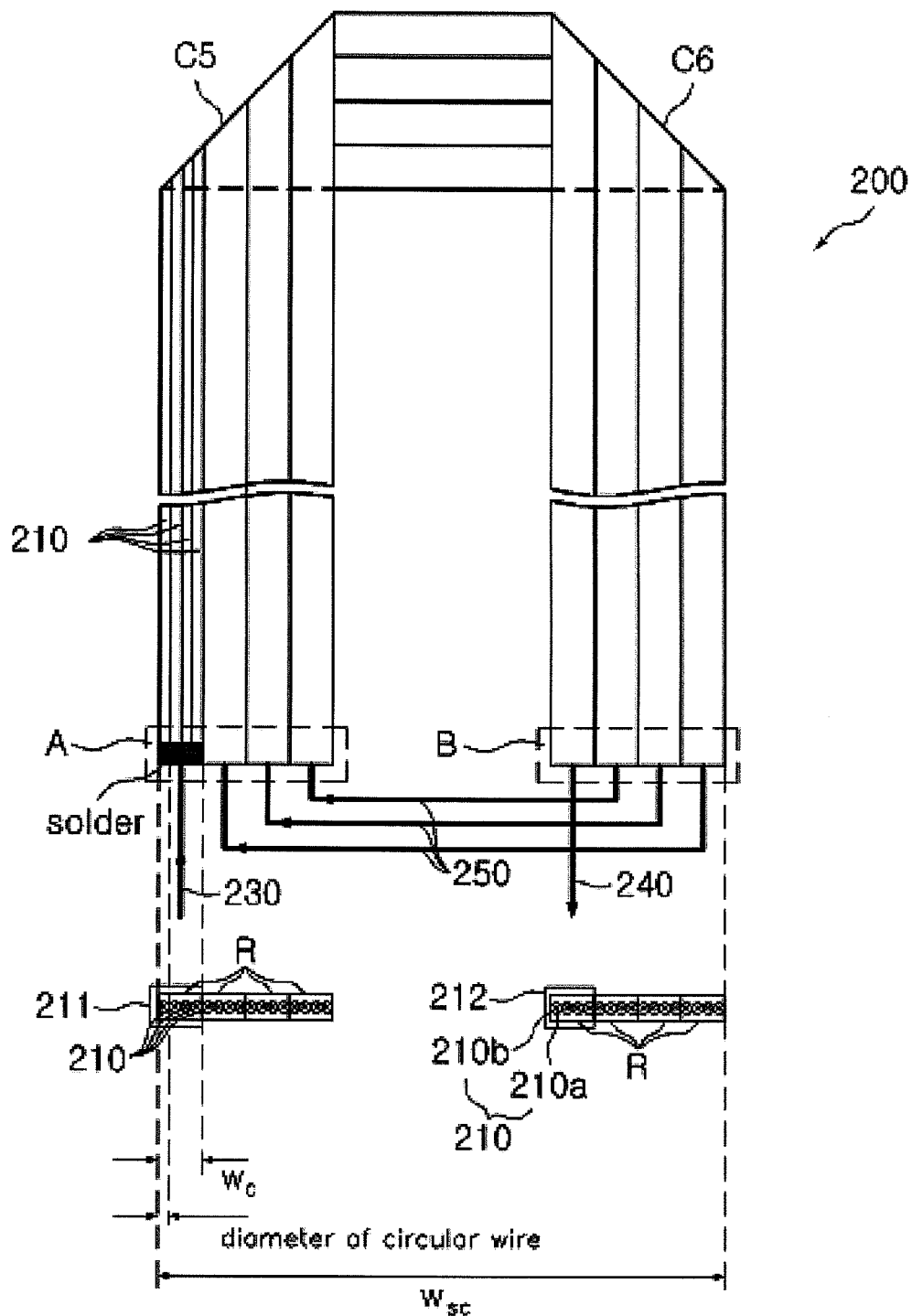
FIG. 7 is a plan view of a spiral coil manufactured according to another embodiment of the present invention.
Figure 8:
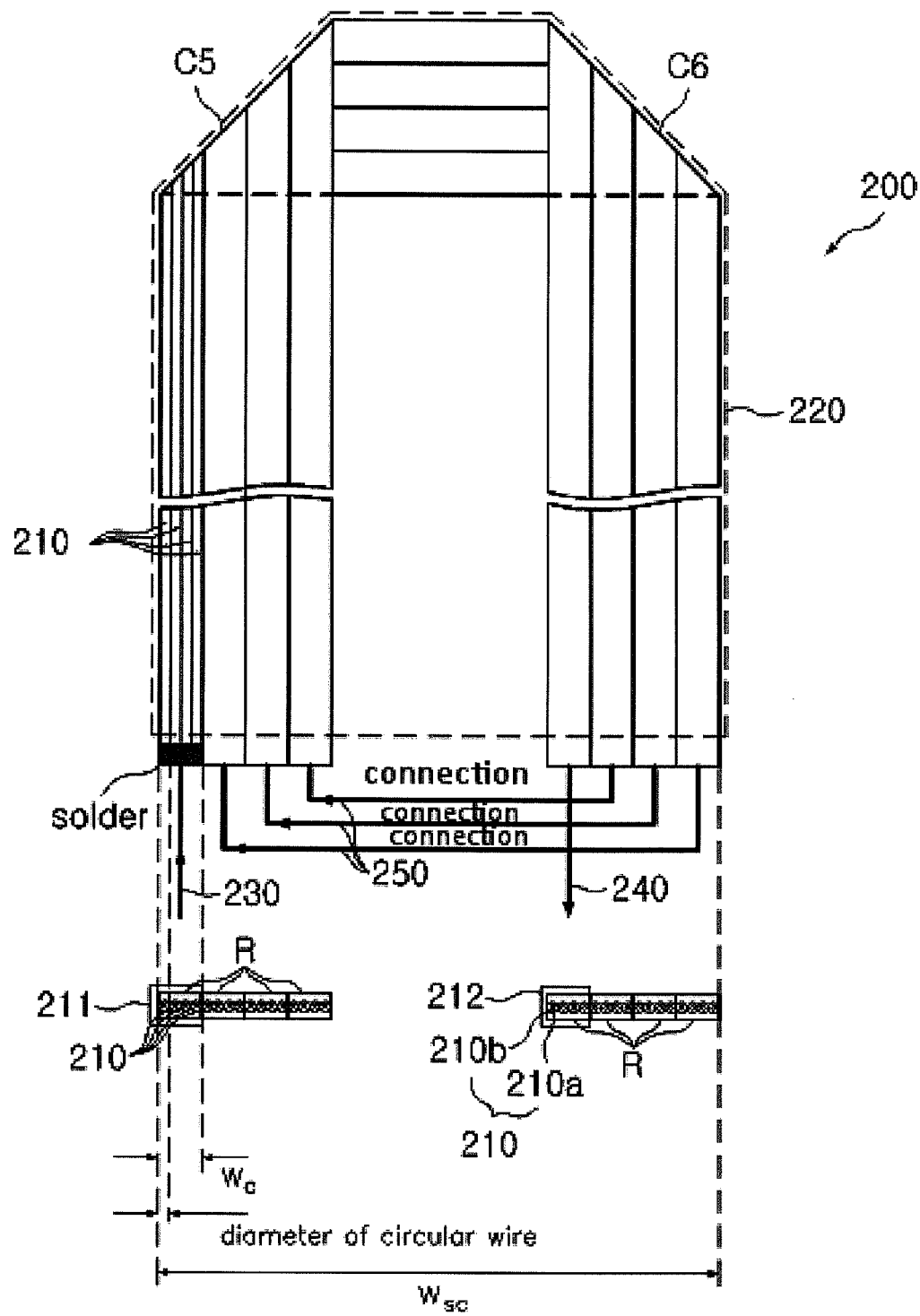
FIG. 8 is a plan view for describing manufacturing processes of the spiral coil of FIG. 7.
Figure 9:
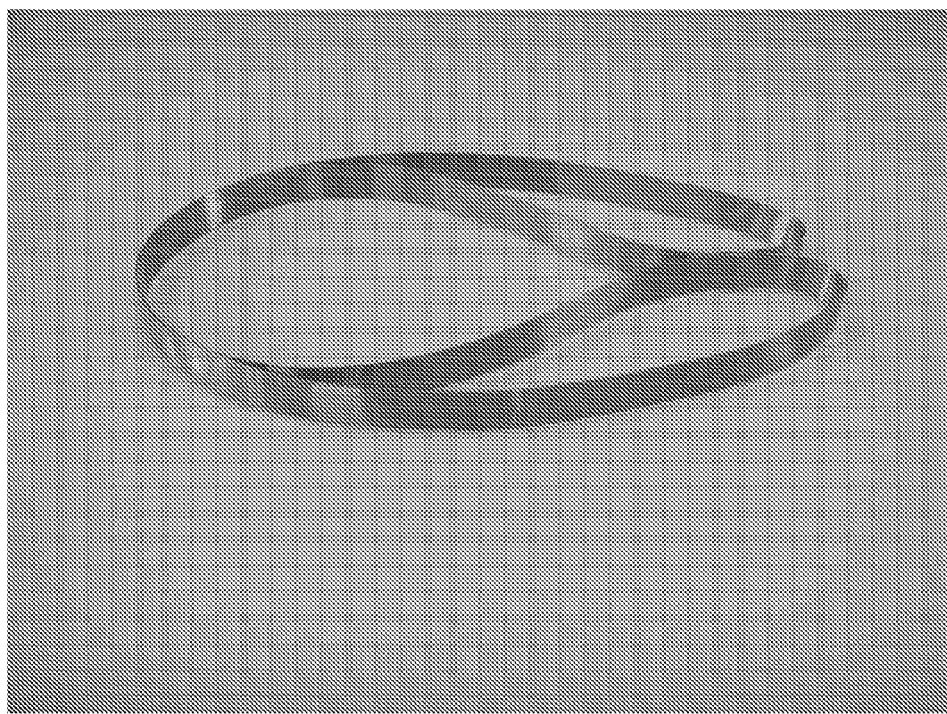
FIG. 9 is a photo of the solenoid manufactured according to the process of FIG. 4.

FIG. 2 is a plan view of a spiral coil 100 manufactured according to an embodiment of the present invention and FIGS. 3A and 3B are respectively a plan view and a front view of a work module for generating the spiral coil 100 of FIG. 2. FIG. 4 is a perspective view for describing a process of forming a solenoid for the spiral coil 100 of FIG. 2 by using the work module of FIG. 3 and FIGS. 5 and 6 are plan views for describing manufacturing processes of the spiral coil 100 of FIG. 2. FIG. 7 is a plan view of a spiral coil 200 manufactured according to another embodiment of the present invention, and FIG. 8 is a plan view for describing manufacturing processes of the spiral coil 200 of FIG. 7. FIG. 9 is a photo of the solenoid manufactured according to the process of FIG. 4.

FIG. 2 shows the spiral coil 100 according to the current embodiment, which has a plane shape and is elongated (has large slenderness). The spiral coil 100 may be manufactured by using a thin rectangular or circular insulated electric wire having an insulated film such as an enamel copper wire. In FIG. 2, a rectangular insulated electric wire 110 is used to manufacture the spiral coil 100. Here, $t_c$ and $W_c$ respectively denote a thickness and width of the insulated electric wire 110. Also, $w_{sc}$ denotes a width of the spiral coil 100, l and $w_l$ respectively denote a leg length and width of the spiral coil 100. b denotes a distance between centers of two coil legs and N denotes a wound number of insulated electric wire 110 forming the spiral coil 100. In FIG. 2, N is 5.

A leg length of an elongated spiral coil used for various electro-magnetic acoustic transducers (EMATs) is much larger than a leg width of the coil. As such, effects of portions excluding two legs of a spiral coil having large slenderness may be ignored with respect to electrical characteristics of the spiral coil. Thus, it enables electrical characteristics of the spiral coil 100 to be easily obtained. For example, a direct current resistance R of the spiral coil 100 may be predicted according to Equation 1 below.

$$R \approx 2\rho Nl/A \quad \text{Equation 1}$$

Here, ρ and A respectively denote specific resistance and a sectional area of the insulated electric wire 110. According to an approach method similar to that in a meanderline or grating coil widely used in EMAT fields, inductance of a spiral coil in air is approximated to Equation 2 below.

$$L \approx \frac{2}{\pi} N^2 \mu_0 l \sum_{n=1,3,5\Lambda}^{\infty} \frac{1}{n} \left( \frac{\sin n\pi w_l/2b}{n\pi w_l/2b} \right)^2 \quad \text{[Equation 2]}$$

Here, $\mu_0$ denotes a dielectric constant of air.

The spiral coil 100 of FIG. 2 is manufactured by folding a flexible solenoid such that an external surface and an internal surface of the spiral coil 100 are changed at four corners C1 through C4. A method for manufacturing the spiral coil 100 of FIG. 2 will now be described in detail.

First, the insulated electric wire 110 having a circular or rectangular shape is spirally wound to form a solenoid having a diameter larger than a length. Referring to FIGS. 3A and 3B, a work module is separately prepared first to form the solenoid. The work module includes a work plate 10 having a plurality of thread grooves 11 along a length direction, and two cylinders 20 each having a screw thread 21 at the end to be lockable to the thread groove 11.

After preparing the work module, the cylinders 20 are strongly locked to two thread grooves 11 having a separation distance corresponding to the leg length l of the spiral coil 100, which are selected from among the thread grooves 11. Then, referring to FIG. 4, the solenoid is formed by tightly and spirally winding the insulated electric wire 110 along the two cylinders 20. The insulated electric wire 110 has two terminals portions 111 and 112 pertaining to start and end points formed while forming the solenoid having a wound shape. Here, a length of the solenoid is predetermined while desining the spiral coil 100.

Next, in order to fix the wound shape of the solenoid, an adhesive tape 30 is adhered along external and internal surfaces of the solenoid. Accordingly, the shape of the wound insulated electric wire 110 may be fixed. FIG. 4 is illustrated as if the adhesive tape 30 is adhered only to the external surface of the solenoid, but it is due to a viewing angle, and the adhesive tape 30 is also adhered to the internal surface of the solenoid.

The adhesive tape 30 may be uniformly adhered to the entire external and internal surfaces of the solenoid by using any one of various methods. However, a taping operation is somewhat difficult due to curved shapes of the cylinders 20 near the cylinders 20. Thus, referring to FIG. 4 as an example of adhering the adhesive tape 30, the adhesive tape 30 is first adhered to the external and internal surfaces of the solenoid corresponding to a region between the two cylinders 20 where the taping operation is relatively easily performed. Here, the adhesive tape 30 is not adhered to the solenoid near the cylinders 20.

Then, when the locking of the cylinders 20 is somewhat loosened, the end locking of the cylinders 20 to the thread grooves 11 is weakened and loosened and the cylinders 20 may be slightly tilted with respect to the thread grooves 11, and thus a distance between the cylinders 20 may be slightly narrowed. Accordingly, the solenoid wound on an outer side of the cylinders 20 is slightly loosened, and the solenoid is rotated based on the cylinders 20 so as to rotate and move the external and internal surfaces of the solenoid, where the adhesive tape 30 is not adhered to because they are located near the cylinders 20, to locations for easy adhesion. Next, the cylinders 20 are again strongly locked, the insulated electric wires 110 of the solenoid where the adhesive tape 30 is not adhered to are arranged to be closely adhered, and then the external and internal surfaces are fixed by using an adhesive tape (not shown). As such, the adhesive tape 30 is adhered to all of the external and internal surfaces of the solenoid. Of course, after the adhesion of adhesive tape 30, an extra adhesive tape left on the edge of the insulated electric wire 110 forming the solenoid may be neatly trimmed by using a heated monofilament wire cuter. FIG. 9 shows an example of a flexible solenoid formed via above operations.

Next, the four corners C1 through C4 in a circumference direction with respect to the solenoid fixed by the adhesive tape 30 are folded on a predetermined flat platform so as to form the spiral coil 100 having a plane shape with folded corners as shown in FIG. 5. Then, the folded corners C1 through C4 are fixed. A fixing process of the folded corners C1 through C4 will now be described with reference to FIGS. 5 and 6.

First, referring to FIG. 5, a bottom surface of the spiral coil 100 having the plane shape is fixed to a top surface of the platform by using a double-sided adhesive tape so that a top surface of the spiral coil 100 is exposed upward. Here, an adhesive tape 30a adhered to the top surface of the spiral coil 100 from among the adhesive tape 30 is carefully removed. Then, a first single-sided adhesive tape 120 is covered on and adhered to the top surface of the spiral coil 100. The first single-sided adhesive tape 120 has a slightly wider width than the spiral coil 100, and may be a polyimide tape or the like having excellent thermal resistance and chemical resistance.

Then, referring to FIG. 6, the spiral coil 100 is removed from the platform, turned over, and then fixed again by a double-sided adhesive tape such that the bottom surface of the spiral coil 100 is exposed upward. Next, an adhesive tape 30b adhered to the bottom surface of the spiral coil 100 from among the adhesive tape 30 is carefully removed. Then, a second single-sided adhesive tape 130 is covered on and adhered to the bottom surface of the spiral coil 100. The second single-sided adhesive tape 130 has the same size and material as the first single-sided adhesive tape 120. Here, strong adhesion between the first and second single-sided adhesive tapes 120 and 130 corresponding to two surfaces of the spiral coil 100 helps the shape of the spiral coil 100 to be maintained long.

Then, the spiral coil 100 is removed from the platform, and then is completed by uniformly and neatly trimming the edges of first and second single-sided adhesive tapes 120 and 130 by using a tape cutter or the like. Here, the terminal portions 111 and 112 corresponding to the start and end points of the spiral coil 100 are connected to a separate connector (not shown), and a bottom portion of the spiral coil 100 including the connector is fixed to a fixing module (not shown) for repeated use, thereby completing the spiral coil 100. The fixing module may be a socket, a fixing case, or the like for fixing the bottom surface of the spiral coil 100 and the connector.

The insulated electric wire 110 having the rectangular shape is suitable in manufacturing a spiral coil having a low wound number and low impedance, whereas an insulated electric wire having a circular shape is suitable in manufacturing a spiral coil having a high wound number and high impedance. A circular insulated electric wire having any diameter may be easily obtained with low cost, but a rectangular insulated electric wire is difficult to be obtained, and thus it is difficult to manufacture a thin spiral coil having low impedance.

Hereinafter, a method for manufacturing the spiral coil 200 that is flexible and has low impedance by using a circular insulated electric wire, according to the other embodiment of the present invention will now be described with reference to FIGS. 7 and 8.

First, an insulated electric wire 210 having a circular shape is spirally wound to form a solenoid having a diameter larger than a length. The solenoid according to the current embodiment may be formed like the solenoid according to the previous embodiment. Also, after forming the solenoid, external and internal surfaces of the solenoid may be fixed by using an adhesive type like the previous embodiment.

Then, referring to FIG. 7, a part of the solenoid is cut along a length direction of the solenoid and two corners C5 and C6 in a circumference direction are folded, thereby forming a U-shaped ribbon cable having a plane shape and folded corners while having cut ends A and B. In detail, the U-shaped ribbon cable having folded corners may be formed by cutting the part of solenoid in the length direction to form a ribbon cable having the two cut ends A and B, and then folding the two corners C5 and C6 with respect to a circumference direction of the ribbon cable.

Then, the folded corners C5 and C6 of the U-shaped ribbon cable are fixed. The folded corners C5 and C6 are fixed according to the method of previous embodiment, by using single-sided adhesive tape 220 to top and bottom surfaces. At this time, the single-sided adhesive tape 220 is used excluding the two cut ends A and B.

During the fixing process with reference to the previous embodiment, the U-shaped ribbon cable is first placed on a flat platform and a bottom surface of the U-shaped ribbon cable is fixed to a top surface of the platform by using a double-sided adhesive tape or the like such that the top surface of the U-shaped ribbon cable is exposed upward. Then, the adhesive tape adhered on the top surface of the U-shaped ribbon cable is carefully removed, and the single-sided adhesive tape 220 is adhered throughout the top surface of the U-shaped ribbon cable.

Then, the U-shaped ribbon cable is removed from the platform, turned over, and then fixed again with a double-sided adhesive tape such that the bottom surface of the U-shaped ribbon cable is exposed upward. Next, the adhesive tape adhered on the bottom surface of the U-shaped ribbon cable is carefully removed, and the single-sided adhesive tape 220 is covered on and adhered to the bottom surface of the U-shaped ribbon cable. Then, the U-shaped ribbon cable is removed from the platform, and an edge of the single-sided adhesive tape 220 is trimmed by using a tape cutter or the like.

As described above, after fixing the folded corners C5 and C6 of the U-shaped ribbon cable, an insulated film 210a at the end of the insulated electric wire 210 of each of the two cut ends A and B is removed. Also, ends of internal wires 210b exposed by removing the insulated film 210a are divided into a plurality of bundles, and the ends of the internal wires 210b are soldered according to bundles such that each bundle forms a quasi-rectangular wire R. Accordingly, the shape of the U-shaped ribbon cable is transformed to a U-shaped ribbon cable formed of the quasi-rectangular wires R.

Then, the quasi-rectangular wires R of the cut end A and the quasi-rectangular wires R of the cut end B are connected according to lines by using a short wire 250 to form a spiral coil. Since a length of a connecting wire is very shorter than a length of entire coil, the short wire 250 is used, and a type of the connecting wire is not limited. Meanwhile, quasi-rectangular wires corresponding to two terminal portions 211 and 212 pertaining to start and end points of the spiral coil are not connected.

Of course, the two terminals portions 211 and 212 may be extended by respectively using short wires 230 and 240 to be used later as terminals. Then, the two terminal portions 211 and 212 (in detail, the terminal portions formed of the short wires 230 and 240) are connected to a separate connector (not shown) and a bottom portion of the spiral coil 200 including the connector is fixed to a fixing module (not shown) for repetitive use, thereby completing the spiral coil 200 that is thin and has low impedance. The spiral coils 100 and 200 having folded corners manufactured as above are used in an EMAT to be accurately operated.

An effectiveness verification result of the spiral coil 200 according to the current embodiment will now be described. 5 spiral coils 200 identically designed are manufactured to measure electric characteristics thereof and compare the electric characteristics with prediction. Design specifications are as follows. A leg length l and width $w_l$ of the spiral coil 200 were respectively 500 mm and 13.7 mm, and a distance b between two coil legs was 28 mm.

Also, following procedures for obtaining a spiral coil having low impedance were applied. A solenoid was formed from a 0.2 mm enamel copper wire, and the spiral coil 200 was manufactured by connecting the quasi-rectangular wires R each formed of 10 enamel copper wires. Thus, the sectional area A of the quasi-rectangular wire R is 10 times of 0.01 $\pi$mm$^2$. Specific resistance $\rho$ of the enamel copper wire was $1.72 \times 10^{-8}$ $\Omega$m, and a wound number N of the spiral coil 200 was 6. A direct current resistance R and inductance L of the spiral coil 200 predicted based on Equations 1 and 2 were respectively 0.33$\Omega$ and 12.3 $\mu$H. Averages of thereof measured by using an LCR meter (Hioki 3235-50) were respectively 0.46 $\Omega$ and 16.3 $\mu$H, with error ranges respectively of $\pm 0.06$ $\Omega$ and $\pm 0.07$ $\mu$H. At this time, a relatively accurate equality result between prediction and measurement may be determined. This suggests that an insulated electric wire is not cut or electrically shorted near folded corners, and the method suggested in the present invention is effective.

According to the methods, a large and thin spiral coil having folded corners is easily manufactured from an insulated electric wire such as an enamel copper wire. Electric characteristics of spiral coils having large slenderness may be interpretively predicted. Spiral wires having various sizes and flexible enough to be not easily damaged due to folding of an insulated film are easily obtained with low costs. The spiral wires enable the use of a surface RF coil optimized to various applications of EMAT. Also, the spiral wires may induce engineers to easily access an optimized transducer.

According to the methods of the present invention, a thin and long spiral coil having folded corners can be easily manufactured by using a general insulated electric wire. In addition, the spiral coil manufactured by using such a method is applicable to a surface radio frequency (RF) coil optimized for various applications of an EMAT and enables easy access to an optimized transducer.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A method for manufacturing a spiral coil, the method comprising:
   forming a solenoid having a diameter larger than a length by spirally winding an insulated electric wire;
   forming a spiral coil having folded corners by folding four corners in a circumference direction with respect to the solenoid;
   fixing the folded corners of the spiral coil; and
   fixing two terminal portions corresponding to start and end points of the spiral coil.

2. The method of claim 1, wherein the insulated electric wire is one circular or rectangular insulated electric wire.

3. The method of claim 1, wherein the forming of the solenoid comprises:
   preparing a work module comprising a work plate having a plurality of thread grooves along a length direction, and two cylinders having screw threads at terminals to be respectively lockable to the plurality of thread grooves;
   respectively locking the two cylinders to two thread grooves having a separation distance corresponding to a leg length of the spiral coil, which are selected from among the plurality of thread grooves;
   forming the solenoid by spirally firmly winding the insulated electric wire along the two cylinders; and
   adhering an adhesive tape along external and internal surfaces of the solenoid so as to fix a wound shape of the solenoid, and
   the forming of the spiral coil having the folded corners comprises forming a spiral coil having a plane shape by respectively folding the four corners in the circumference direction with respect to the solenoid fixed by the adhesive tape.

4. The method of claim 3, wherein the fixing of the folded corners of the spiral coil comprises:
   exposing a top surface of the spiral coil upward by fixing a bottom surface of the spiral coil having the plane shape to a top surface of a platform;
   removing a part of the adhesive tape, which is adhered to the top surface of the spiral coil;
   covering and adhering a first single-sided adhesive tape to the top surface of the spiral coil;
   exposing a bottom surface of the spiral coil upward by turning over the spiral coil at the platform;
   removing a part of the adhesive tape, which is adhered to the bottom surface of the spiral coil;

covering and adhering a second single-sided adhesive tape to the bottom surface of the spiral coil; and completing the spiral coil by removing the spiral coil from the platform and then trimming edges of the first and second single-sided adhesive tapes.

* * * * *

UNITED STATES PATENT AND TRADEMARK OFFICE
CERTIFICATE OF CORRECTION

| | | |
|---|---|---|
| PATENT NO. | : 8,661,654 B2 | Page 1 of 1 |
| APPLICATION NO. | : 13/320615 | |
| DATED | : March 4, 2014 | |
| INVENTOR(S) | : Myoung Seon Choi, Sung Joon Kim and Won Nyoung Heo | |

It is certified that error appears in the above-identified patent and that said Letters Patent is hereby corrected as shown below:

Title Page, item (73), in the Assignee section, please delete "Industry-Academic Cooperation Foundation, Yeungnam University, Gyeongsan-Si, Gyeongsangbuk-Do (KR)" and insert --Industry-Academic Cooperation Foundation, Yeungnam University, Gyeongsan-Si, Gyeongsangbuk-Do (KR), DIGITAL ULTRASONICS CO., LTD., Gyeongsan-si, Gyeongsangbuk-do (KR)--.

Signed and Sealed this
Thirtieth Day of September, 2014

Michelle K. Lee
*Deputy Director of the United States Patent and Trademark Office*